(12) United States Patent
Settke et al.

(10) Patent No.: US 12,102,546 B2
(45) Date of Patent: Oct. 1, 2024

(54) DEVICE AND A METHOD FOR PREPARING A BONE TRANSPLANT

(71) Applicant: MATHYS AG BETTLACH, Bettlach (CH)

(72) Inventors: Alexander Settke, Jena (DE); Claudia Hesky, Jena (DE); Frank Dallmann, Schmölln (DE)

(73) Assignee: MATHYS AG BETTLACH, Bettlach (CH)

( * ) Notice: Subject to any disclaimer, the term of this patent is extended or adjusted under 35 U.S.C. 154(b) by 39 days.

(21) Appl. No.: 17/780,413

(22) PCT Filed: Nov. 30, 2020

(86) PCT No.: PCT/EP2020/083860
§ 371 (c)(1),
(2) Date: May 26, 2022

(87) PCT Pub. No.: WO2021/105495
PCT Pub. Date: Jun. 3, 2021

(65) Prior Publication Data
US 2023/0000646 A1 Jan. 5, 2023

(30) Foreign Application Priority Data
Nov. 29, 2019 (DE) ..................... 10 2019 132 412.2

(51) Int. Cl.
*A61F 2/46* (2006.01)
(52) U.S. Cl.
CPC .................. *A61F 2/4644* (2013.01)
(58) Field of Classification Search
CPC ............................. A61B 17/15; A61F 2/4644
See application file for complete search history.

(56) References Cited

U.S. PATENT DOCUMENTS

| | | | | |
|---|---|---|---|---|
| 2,003,619 A | * | 6/1935 | Williamson | B23D 51/04 269/287 |
| 4,565,192 A | * | 1/1986 | Shapiro | A61B 17/1604 606/88 |

(Continued)

FOREIGN PATENT DOCUMENTS

WO 2021105495 A1 6/2021

OTHER PUBLICATIONS

Examiner Figure G (Year: 2024).*

(Continued)

*Primary Examiner* — Michael W Hotchkiss
(74) *Attorney, Agent, or Firm* — Nixon Peabody LLP (57) ABSTRACT

The device according to the invention for preparing a bone transplant (100) outside the human or animal body comprises a base element (101) and at least one holding element (102). The at least one holding element (102) is inserted in the base element (101) of the device for preparing a bone transplant (100). In the method according to the invention for configuration of the device according to the invention, the at least one holding element (102) is inserted into the base element of the device for preparing a bone transplant (100). In the method according to the invention for preparing a bone transplant outside the human or animal body with the device according to the invention (100), a bone fragment to be prepared is placed into the holding element (102) inserted in the base element (100), the bone fragment to be prepared is fixed with the inserted holding element, and the bone fragment to be prepared is processed.

13 Claims, 10 Drawing Sheets

(56) References Cited

U.S. PATENT DOCUMENTS

| | | | | |
|---|---|---|---|---|
| 6,676,662 B1* | 1/2004 | Bagga | A61F 2/4644 | 606/87 |
| 7,802,503 B2* | 9/2010 | Couvillion | B26D 7/02 | 83/762 |
| 8,127,646 B2* | 3/2012 | Couvillion | B26D 7/02 | 83/34 |
| 8,430,880 B2* | 4/2013 | Gil | A61B 17/1635 | 30/282 |
| 8,800,158 B1* | 8/2014 | Shim | A61F 2/4644 | 33/630 |
| 9,566,718 B2* | 2/2017 | Kloiber | B23D 55/082 | |
| 9,700,438 B2* | 7/2017 | Kehres | B25B 5/163 | |
| 11,213,406 B2* | 1/2022 | Rodriguez | A61F 2/4644 | |
| 2002/0082604 A1* | 6/2002 | Abdelgany | A61F 2/4644 | 623/16.11 |
| 2002/0138078 A1* | 9/2002 | Chappuis | A61B 17/1671 | 606/85 |
| 2004/0034360 A1* | 2/2004 | Dalton | A61F 2/4644 | 606/87 |
| 2004/0034361 A1* | 2/2004 | Dalton | A61B 17/15 | 606/87 |
| 2008/0215052 A1* | 9/2008 | Steiner | A61F 2/4644 | 606/53 |
| 2012/0191093 A1* | 7/2012 | Wong | A61B 17/1635 | 606/79 |
| 2012/0253350 A1* | 10/2012 | Anthony | A61B 17/14 | 606/87 |
| 2017/0056085 A1* | 3/2017 | Provencher | A61B 17/8863 | |
| 2019/0209186 A1 | 7/2019 | Guilloux et al. | | |
| 2021/0007863 A1* | 1/2021 | Rodriguez | A61F 2/4644 | |

OTHER PUBLICATIONS

International Search Report and Written Opinion for related International Application PCT/EP2020/083860, dated Feb. 17, 2021, 12 pages.

* cited by examiner

DEVICE AND A METHOD FOR PREPARING A BONE TRANSPLANT

A device and a method for preparing a bone transplant The present application is a U.S. national phase entry of PCT/EP2020/083860, filed on Nov. 30, 2020, which claims priority to German Patent Application No. 10 2019 132 412.2, filed on Nov. 29, 2019, which are incorporated herein by reference in their entirety.

The invention relates to a device for preparing a bone transplant for insertion into a human or animal bone and an associated method for configuration of the device.

Diseases, accidents and signs of wear from overloading can damage joints of the human or animal body. If the joints cannot be healed using conservative methods, it may become necessary to replace the joint. In the human body, it is often necessary to replace damaged shoulder joints, hip joints or knee joints with replacement joint implants. Various methods for the implantation of artificial joints are available dependent upon the joint affected. In some cases, a so-called inverse shoulder prosthesis is used in the shoulder joint region. Inverse shoulder prostheses are characterised in that the artificial joint socket replaces the damaged humeral head and the artificial joint head replaces the damaged glenoid.

One peculiarity of modern inverse shoulder prostheses is the use of bone transplants in the glenoid region. The use of a bone transplant allows a secure fixing of an implant despite bone loss.

In general, the bone transplant used is obtained from the humeral head of the operated shoulder. For this purpose, a guide wire is positioned in the humeral head by means of a positioning instrument. In a next step, the surface of the bone transplant is milled flat. In this context, residues of cartilage and the hard bony parts of the humeral head are removed. Using a core drill, the bone to be extracted is separated at its lateral edges from the humeral head. A hole is then drilled into the bone fragment to be extracted, so that the guide wire is removed at the same time. Separation of the bone fragment to be extracted at its lateral edges and drilling can be implemented in one operating stage by using a core drill with integrated central drill. In the last step of the extraction, a cutting guide instrument is used. This cutting guide instrument is embodied in such a manner that it is placed with an exact fit on the milled surfaces. A bone saw is guided in a slot within the cutting guide instrument in such a manner that the bone transplant to be extracted is resected with a specified angle. Other variants of the cutting guide tools contain a plateau for guiding the bone saw. In this context, the bone saw is guided by unilateral support against the plateau.

US 2019/020 9186 A1 describes such a cutting guide instrument for extracting a bone transplant. The cutting guide instrument contains a base plate which is placed onto the bone fragment to be extracted. Furthermore, the cutting guide instrument contains a saw guide which is designed to receive and to guide a saw blade of a bone saw. This saw guide is connected to the base plate via a depth flange with a spacing distance.

With this cutting guide instrument for the extraction of a bone transplant, it is disadvantageous that the cutting guide instrument is used in the patient's body. As a result of the type of guiding of the saw blade, especially the unilateral guide, a dimensional accuracy of the extracted bone transplant is low.

The invention is therefore based on the object of providing a device for extracting a bone transplant of a human or animal bone and an associated method for configuring the device, without the need to consider the disadvantages mentioned.

The object is achieved in an advantageous manner by a device according to the invention for preparing a bone transplant outside the human or animal body according to claim 1 and by a method for configuring the device outside the human or animal body according to claim 11. Advantageous further developments form the subject matter of the dependent claims relating back to these claims.

The device according to the invention for preparing a bone transplant outside the human or animal body comprises a base element and at least one holding element. The at least one holding element is inserted into the base element of the device for preparing a bone transplant. A bone transplant which has previously been removed from the body can be held in a particularly advantageous manner for the preparation by the holding element disposed in the base element. Secure holding of the bone transplant in a precisely specified position is achieved by the holding element. Only this secure holding of the bone transplant with the holding device can ensure an extremely accurate processing of the bone transplant.

Advantageously, the device for preparing a bone transplant preferably comprises a first holding element and a second holding element, wherein the first holding element is a guide insert and the second holding element is a holding insert. In a particularly advantageous manner, the bone transplant to be prepared is guided securely in its position by the guide insert and fixed in this position by the holding insert.

In an advantageous manner, the base element preferably comprises at least one slot for guiding a material-removing tool. By means of the at least one slot, the material-removing tool is guided in such a manner that the position and the angle specified by the slot are observed accurately.

Advantageously, the guide insert comprises a contact surface, which preferably comprises an angle relative to the slot for guiding the material-removing tool. The holding insert preferably comprises an angle corresponding to the angle of the guide insert relative to the slot for guiding the material-removing tool. The contact surface of the guide insert arranged at an angle allows the precise processing of the extracted bone fragment while observing the specified angle. With an appropriate angle of the holding insert, it is possible to fix the bone fragment in such a manner that, during the entire cutting process, no change of angle can occur.

Advantageously, the guide insert preferably comprises a further contact surface with a further, different angle relative to the slot for guiding the material-removing tool. Furthermore, the holding insert preferably comprises a further angle corresponding to the angle of the guide insert relative to the slot for guiding the material-removing tool. In this manner, it is possible with only one device for the preparation of a bone transplant, to prepare bone fragments with different cutting angles.

In an advantageous manner, the contact surface and the further contact surface(s) of the guide insert are arranged opposite one another. Such an arrangement allows the user to adapt the cutting parameters simply by turning the guide insert to the specifications for the prosthesis.

Advantageously, the holding insert preferably comprises at least two guides, wherein the at least two guides are embodied geometrically differently. Correspondingly, the base element preferably contains at least two guide receivers for receiving the guides of the holding insert. The different embodiment of the two guides prevents the holding insert from being inserted incorrectly. This considerably improves the safety of the process.

It is also advantageous that the holding insert preferably contains at least one finger recess. The finger recess allows the application of an increased thrust to the holding insert. Accordingly, a reliable holding force is exerted on the bone transplant. Furthermore, the risk of the preparer's finger slipping is significantly reduced by the finger recess.

Advantageously, the guide insert preferably contains at least one semi-circular or semi-cylindrical recess for receiving the bone transplant, of which the axis is arranged at right angles to the contact surface of the guide insert. This guarantees a secure positioning of the extracted bone fragment in the required position in the device for preparing a bone transplant.

It is further advantageous if the guide insert preferably contains a further semi-circular or semi-cylindrical recess for receiving the bone transplant, of which the axis is arranged at right angles to the further contact surface of the guide insert. This arrangement allows bone transplants with a different geometry to be prepared by inserting the guide insert correspondingly into the base element.

In the method for configuring the device for the preparation of a bone transplant outside the human or animal body, the at least one holding element is inserted into the base element of the device for preparing a bone transplant.

It is further advantageous if, in the method for configuring a device for the preparation of a bone transplant, a guide insert of the first holding element is preferably inserted into the base element, and that a holding insert of the second holding element is inserted into the base element. This allows the device for preparing a bone transplant to be assembled in a configuration adapted to the implant.

Accordingly, during the preparation of a bone transplant outside the human or animal body with the device according to the invention, a bone fragment to be prepared can be placed into the at least one holding element inserted in the base element, the bone fragment to be prepared can be fixed with the at least one inserted holding element and the bone fragment to be prepared can be processed. This allows the bone transplant to be prepared for the patient in a particularly safe and accurate manner.

Exemplary embodiments of the device according to the invention for preparing a bone transplant outside the human or animal body and the associated method are explained in greater detail based on the following description. The drawings show.

In all the figures, parts corresponding to one another have been provided with the same reference numbers.

Figure 1:
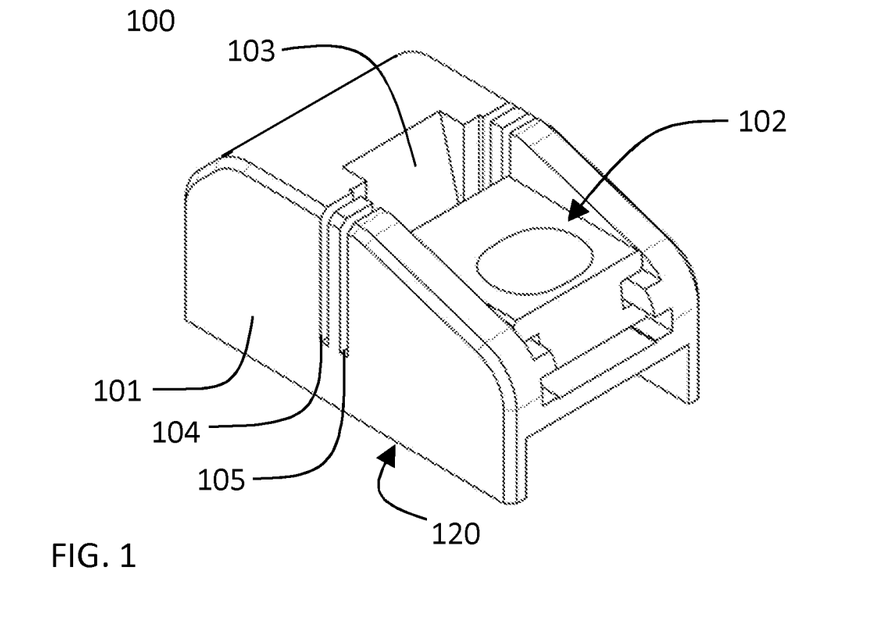
FIG. 1 an exemplary embodiment of a device according to the invention for preparing a bone transplant with a holding element in perspective view.

FIG. 1 shows an exemplary embodiment of a device according to the invention for preparing a bone transplant 100. The device for preparing a bone transplant 100 comprises a base element 101 and a holding element 102. The holding element 102 is inserted into the base element 101. In this exemplary embodiment, the holding element 102 can be pushed into the base element 101 from the front. A contact surface 103 is provided in the base element 101 to receive the bone fragment to be prepared. Furthermore, slots 104, 105 are cut into the base element 101. These slots 104, 105 extend perpendicular to the support surface 120 of the base element 101. In FIG. 1, two slots 104, 105 are illustrated by way of example. However, the base element can be provided with an arbitrary number of slots.

To prepare a bone transplant, an extracted disc of bone is inserted into the base element 101 along the contact surface 103. This extracted bone disc is fixed in position by means of the holding element 102. Dependent upon the required disc thickness of the bone transplant, a cutting tool is guided within one of the two slots 104, 105.

After the bone transplant has been prepared, the holding element 102 can be removed from the base element 101. The individual parts of the device for preparing a bone transplant 100 can therefore be cleaned in a particularly easy manner. Furthermore, this simplifies the checking of the cleaning results, because the contact surface 103 can be readily inspected.

Figure 2:
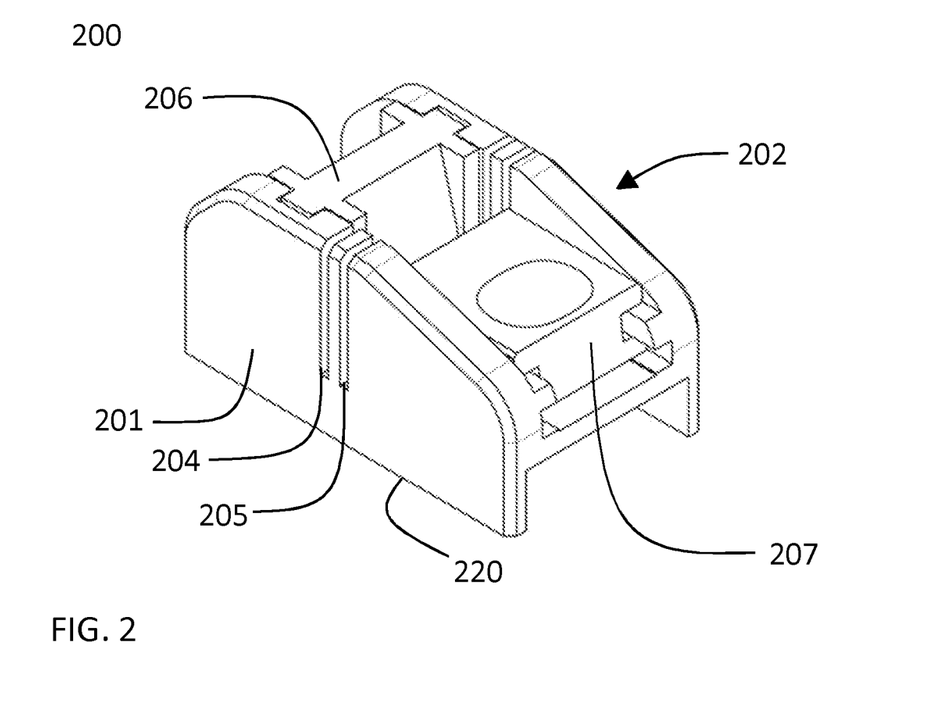
FIG. 2 a second exemplary embodiment of the device according to the invention for preparing a bone transplant with a guide insert and a holding insert in perspective view.

FIG. 2 shows a second exemplary embodiment of a device according to the invention for preparation of a bone transplant 200. The device for preparing a bone transplant 200 of the second exemplary embodiment consists of a base element 201 and two holding elements 202. The first holding element 202 is a guide insert 206. The second holding element 202 is a holding insert 207. The components of the device for preparing a bone transplant 200 of the second exemplary embodiment are described in greater detail in the following.

Figure 3:
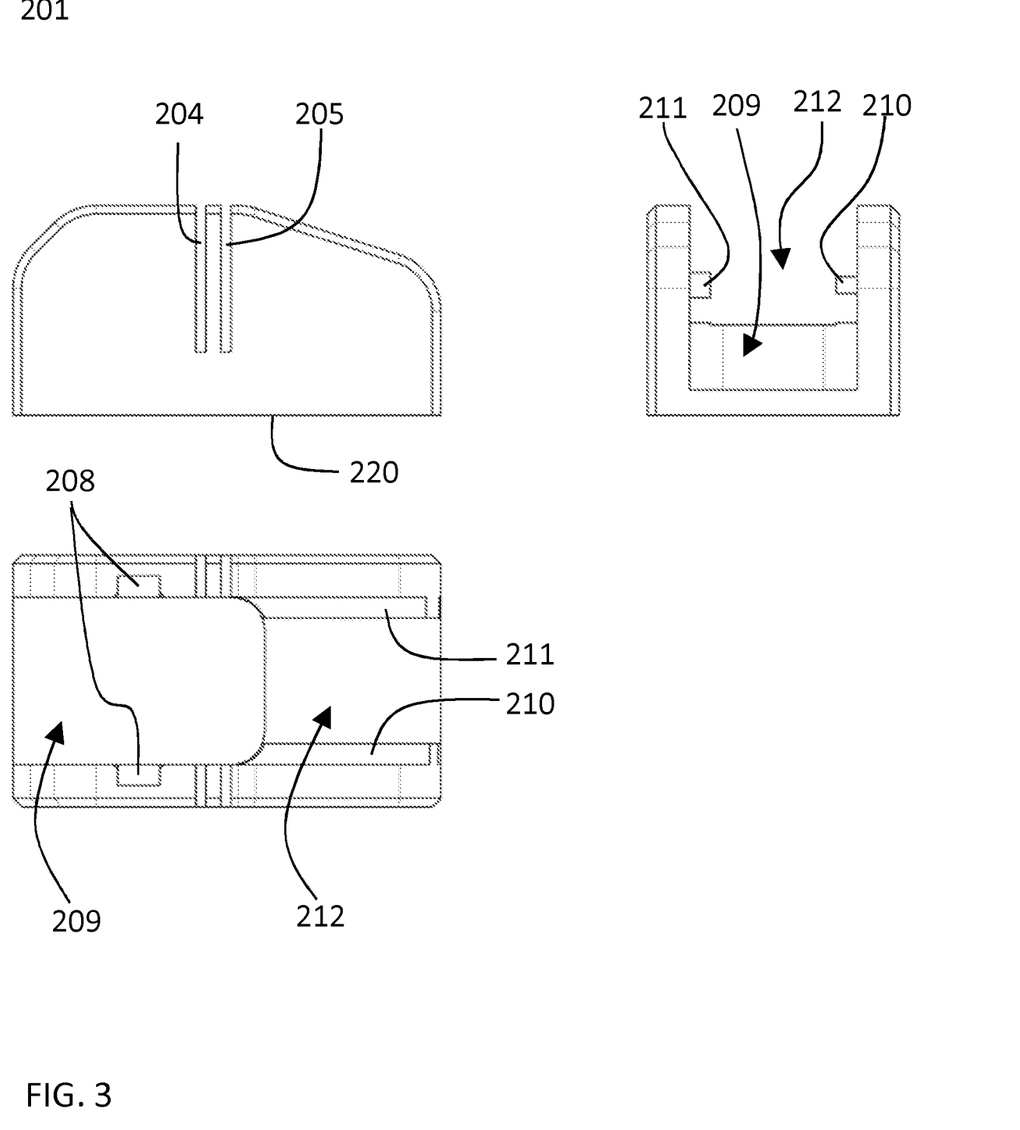
FIG. 3 the base element of the second exemplary embodiment of the device for preparing a bone transplant in a 3-view projection.

FIG. 3 shows a base element of the second exemplary embodiment of a device for preparing a bone transplant 200 in 3-view projection. For improved visual clarity, the reference numbers have not been repeated in each view of the 3-view projection unless this is necessary for an understanding of the drawings.

The front view illustrated in FIG. 3 shows the base element 201 with two slots 204 and 205. These slots 204, 205 extend perpendicular to the support surface 220 of the base element 201. FIG. 3 shows two slots 204, 205 by way of example. However, the base element 201 can contain any number of slots required. The first slot 204 is used if a thin bone transplant is to be prepared. The second slot 205 is provided for thick bone transplants.

The base element 201 contains two recesses 208. These recesses 208 are illustrated in the top view of the base element 201. These recesses 208 can be embodied in the shape of grooves (as shown in FIG. 3) or in a semi-circular manner. Any other required shapes for the recesses 208 are also conceivable. These recesses 208 are used as guides for the guide insert 206 (not shown here).

Furthermore, in the region in which the guide insert 206 can be inserted, the base element 201 contains an indentation 209. The indentation 209 makes available the space for the guide element 206 (not shown here) in the base element 201.

FIG. 3 shows two guide recesses 210, 211, provided in the base element 201. These guide recesses 210, 211 are provided in the longitudinal direction in the region of a recess 212 for receiving the holding insert 207 (not shown here) in the base element 201. As shown, the two guide recesses 210, 211 differ in shape. In the case illustrated here, the left guide recess 210 is significantly higher than the right guide recess 211. Through these different embodiments of the two guide recesses 210, 211, it can be ensured that the holding insert 207 (not shown here) can be inserted into the base element 201 only in the correct position.

The base element 101, 201 of the device for preparing a bone transplant 100, 200 is made of metal or synthetic material. By preference, the base element 101, 201 is made from a stainless steel. If the base element 101, 201 is made from a synthetic material, a PA (polyamide), a PEEK (polyether ether ketone), a PPSU (polyphenylene sulfone) or a POM-C (polyoxymethylene copolymer) is used. These materials are named only by way of example and do not restrict the possible choice of materials.

Figure 4:
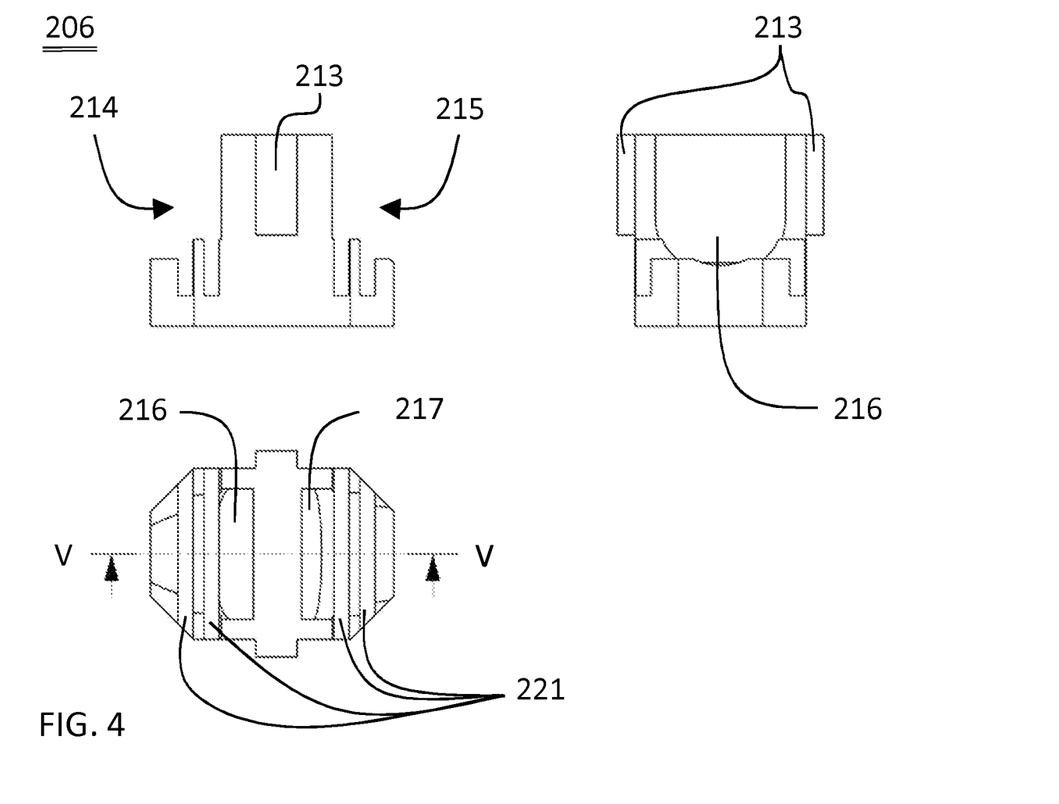
FIG. 4 the guide insert of the second exemplary embodiment of the device for preparing a bone transplant in 3-view projection.
Figure 5:
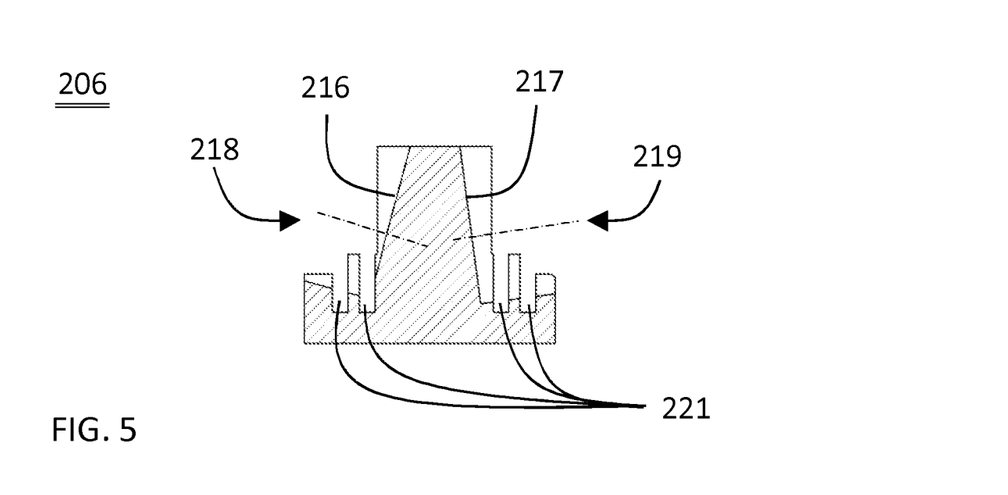
FIG. 5 the guide insert of the second exemplary embodiment of the device for preparing a bone transplant in a sectional view.

FIG. 4 shows a guide insert 206 of the second exemplary embodiment of a device for preparing a bone transplant 200 in 3-view projection. For further visualisation of the guide insert 206, FIG. 5 shows an associated sectional view, wherein the section surface in FIG. 4 is marked with the section line V-V.

The guide insert 206 contains two guide recesses 213. These guide recesses 213 are embodied in such a manner that they form a precisely fitting, displaceable connection with the recesses 208 of the base element 201.

For guiding the bone fragment to be prepared, the guide insert 206 contains a semi-circular recess 214, 215 on each of two opposite sides. The diameter of the semi-circular recess 214, 215 corresponds to the diameter of the bone fragment to be prepared. If the bone transplant is prepared from the entire humeral head, the diameter of the semi-circular recess 214, 215 is adapted to the diameter of the humeral head. The semi-circular recesses 214, 215 each end at a contact surface 216, 217. The axis 218, 219 of the semi-circular recess 214, 215 is aligned at right angles to the associated contact surface 216, 217. The contact surface 216, 217 of the guide insert comprises an angle relative to the slot 204, 205 (not shown here) for guiding the cutting tool in the base element 201.

To prevent damage to the guide insert 206 during preparation of the bone transplant, slots 221 are cut into the guide insert 206. The slots 221 are arranged in such a manner that the slots 221 are disposed in the two installation positions of the guide insert 206 in a precisely fitting manner relative to the slots 204, 205 (not shown here) of the base element 201.

The guide insert 206 is made of metal or synthetic material. By preference, the guide insert 206 is made from stainless steel. If the guide insert 206 is made from synthetic material, here also, a PA (polyamide), a PEEK (polyether ether ketone), a PPSU (polyphenylene sulfone) or a POM-C (polyoxymethylene copolymer) is used. These materials are named only by way of example and do not restrict the possible choice of materials.

FIG. 5 also clearly illustrates that the contact surface 216, 217 of the guide insert 206 in each case comprises an angle relative to the slots for guiding the cutting tool 204, 205 in the base element 201. Dependent upon the requirements for the bone transplant, the angle of the contact surface 216, 217 can comprise an angle between 0° and 45°. Regarding the guide insert 206 in this exemplary embodiment, the contact surface on one side 217 preferably has an angle of 7.5°, and the contact surface on the opposite side 216 preferably has an angle of 15°.

Figure 6:
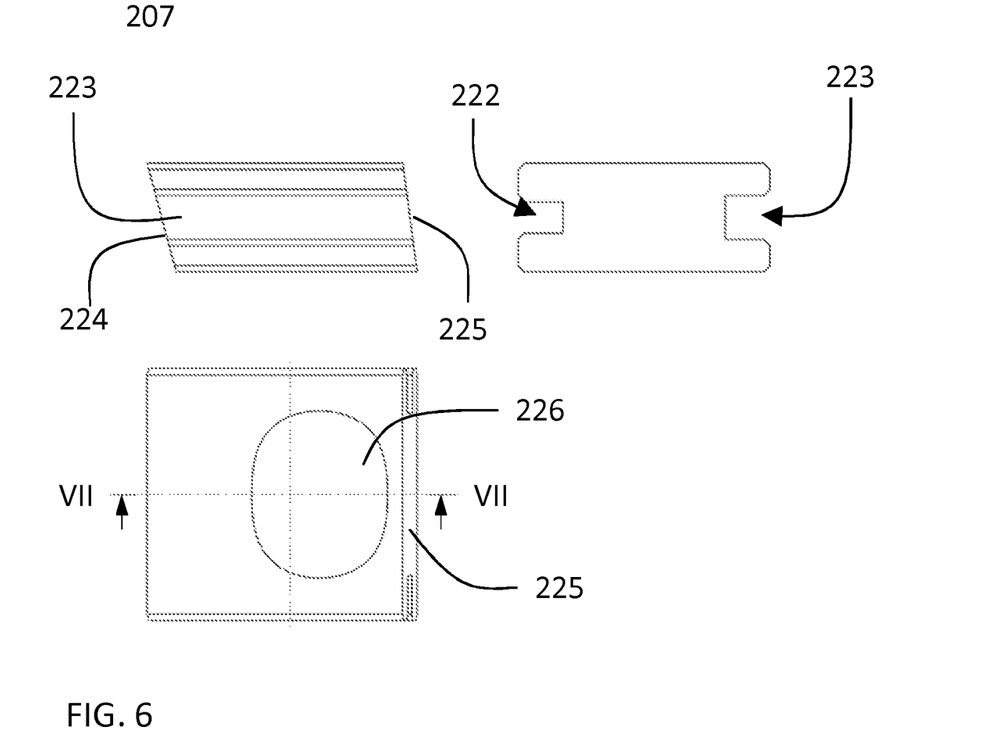
FIG. 6 the holding insert of the second exemplary embodiment of the device for preparing a bone transplant in 3-view projection.
Figure 7:
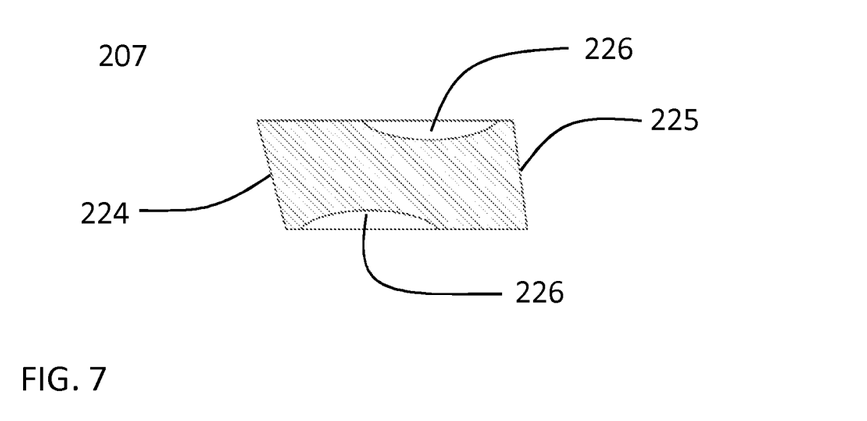
FIG. 7 the holding insert of the second exemplary embodiment of the device for preparing a bone transplant in a sectional view.

FIG. 6 and FIG. 7 show a holding insert 207 of the second exemplary embodiment of a device for preparing a bone transplant 200. FIG. 7 shows the holding insert 207 in a sectional view, wherein the sectional plane is marked in FIG. 6 with the section line VII-VII. Here, the holding insert 207 preferably contains at least two guides 222, 223, which are formed geometrically differently, so that, together with the guide recesses 210, 211 of the base element 201 described above, they form a displaceable connection. By preference, the displaceable connection is embodied according to the Poka Yoke principle. Displaceable connections according to the Poka Yoke principle can be pushed into one another exclusively in the correct position.

The front surfaces 224, 225 of the holding insert 207 are each embodied corresponding to the guide insert 206 with an angle relative to the slot for guiding the cutting tool 204, 205 in the base element 201. Dependent on the corresponding angle of the guide insert 206, an angle of the front surface 224, 225 can comprise an angle between 0° and 45°. By preference, a first front surface 225 comprises an angle of 7.5° and the opposite, second front surface has an angle of 15°.

The surface of the holding insert 207 preferably contains at least one finger recess 226. The finger recess 226 is formed in such a manner that it accommodates one fingertip or several fingertips of the user. The finger recess 226 can also be embodied in such a manner that, for larger holding forces, a ball of the hand or other appropriate body parts can gain a hold within it. The object of the finger recesses 226 is to prevent slipping of the fingers during the processing step. On the one hand, this reduces the risk of injury and on the other hand, the danger of contamination through contact with the bone transplant is reduced.

The holding insert 207 of the device for preparing a bone transplant 200 is made from metal or synthetic material. By preference, the holding insert 207 is made from a stainless steel. If the holding insert 207 is made from a synthetic material, here also a PA (polyamide), a PEEK (polyether ether ketone), a PPSU (polyphenylene sulfone) or a POM-C (polyoxymethylene copolymer) is used. These materials are named only by way of example and do not restrict the possible choice of materials.

Figure 8:
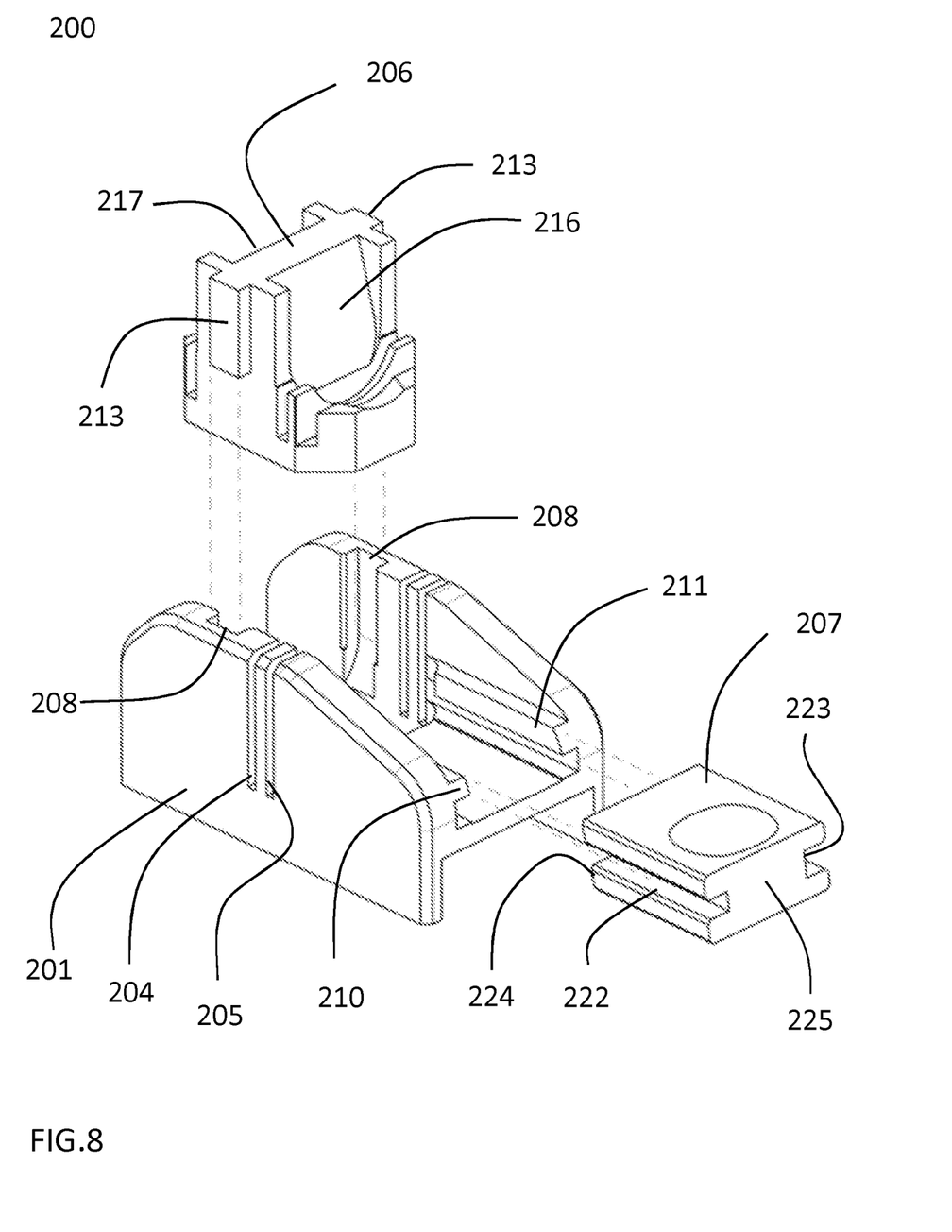
FIG. 8 the second exemplary embodiment of the device according to the invention for preparing a bone transplant with a guide insert and a holding insert in an exploded view.

FIG. 8 shows the second exemplary embodiment of the device according to the invention for preparing a bone transplant 200. Based on this exploded diagram, we explain in the following the method for configuring the device according to the invention for preparing a bone transplant 200. Prior to the preparation of a bone fragment, the components of the device for preparing the bone transplant 200 are assembled as follows:

In a first step, the guide insert 206 is inserted into the base element 201. This is implemented by inserting the guide insert 206 with its two guide recesses 213 into the recesses 208 of the base element 201 provided for this purpose. In this context, the contact surface 216, 217 with the required angle is orientated in such a manner that it faces towards the slots 204, 205 for guiding the cutting tool in the base element.

In a second step, the holding insert 207 is inserted into the base element 201. In this context, the holding insert 207 is positioned in such a manner that the end surface 224, 225 is orientated with the required angle in the direction of the guide insert 206. The geometry of the guides 222, 223 of the holding insert 207 in conjunction with the geometry of the guide recesses 210, 211 ensure that the holding insert 207 cannot be inserted the wrong way round. If a holding insert 207 inserted incorrectly were to be pressed against the bone fragment, the bone fragment could be damaged by an inaccurate cutting guide or the impact of a punctual force and could possibly be rendered unusable.

Figure 9:
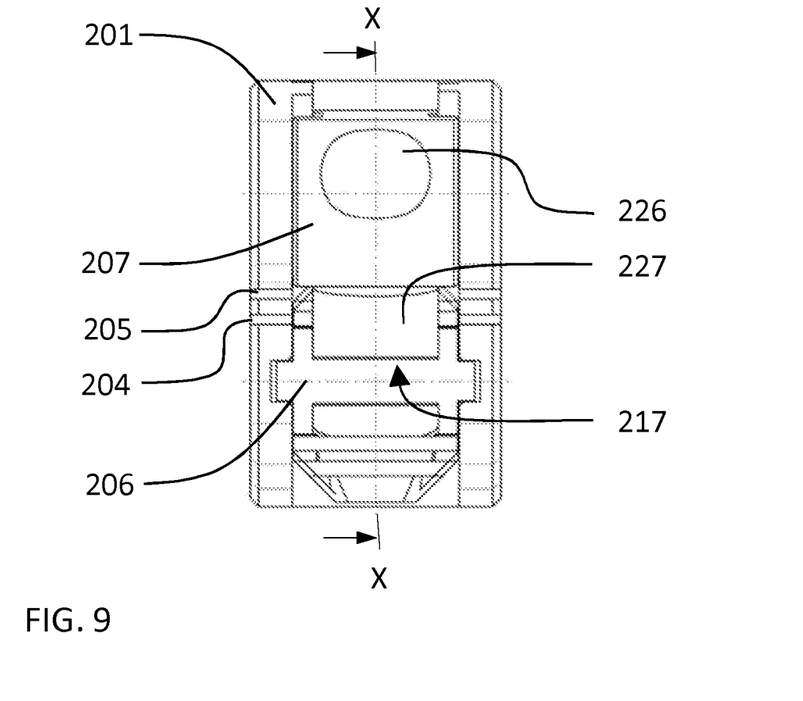
FIG. 9 the second exemplary embodiment of the device according to the invention for preparing a bone transplant with a guide insert and a holding insert and inserted bone transplant in a top view.

FIG. 9 shows the second exemplary embodiment of the device according to the invention for preparing a bone transplant 200 with a positioned bone transplant 227. The bone transplant 227 to be prepared is supported flat on the contact surface 217 of the guide insert 206. By means of the holding insert 207, the bone transplant 227 is pressed against the contact surface 217. For this purpose, the user pushes the holding insert 207 with the help of the finger recess 226 in the direction towards the guide insert 206. During the processing of the bone transplant 227, the user holds the bone transplant 227 firmly on the holding insert 207. The preparation, i.e. the cutting to size of the bone transplant 227 takes place via one of the slots 204, 205 in the base element 201. The slot 204, 205 to be used is selected corresponding to the specifications for the bone transplant 227.

Figure 10:
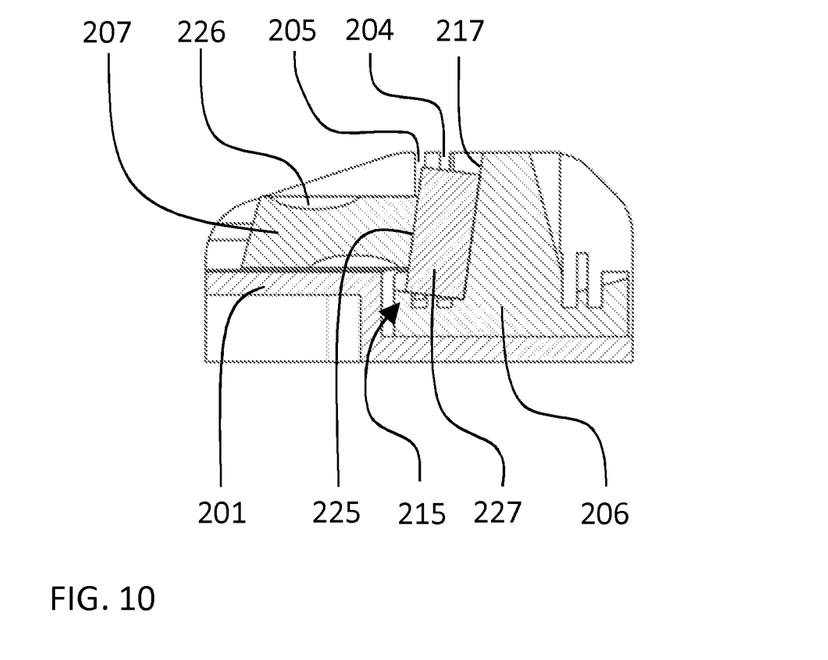
FIG. 10 the second exemplary embodiment of the device according to the invention for preparing a bone transplant with a guide insert and a holding insert and positioned bone transplant in sectional view.

By way of further explanation, FIG. 10 shows the second exemplary embodiment of the device for preparing a bone transplant 200 with positioned bone transplant 227 in sectional view. The sectional plane is marked in FIG. 9 with the section line X-X. It is evident here how the support surface 215 of the semi-circular recess is orientated at right angles to the associated contact surface 217. Accordingly, the bone transplant 227, which is cylindrical before the preparation, is positioned accurately. In this example, the device for preparing a bone transplant 200 is configured in such a manner that the smaller of the two possible angles for processing is used. The guide insert 206 is inserted in such a manner that the contact surface 217 points with the smaller angle in the direction towards the slot 204, 205 of the base element 201. Correspondingly, the holding insert 207 is inserted in such a manner that its front surface 225 is supported with the smaller of the two possible angles on the bone transplant 227. By means of the finger recess 226, the holding insert 207 is pushed in the direction towards the bone transplant 227 and held firmly by it.

Figure 11:
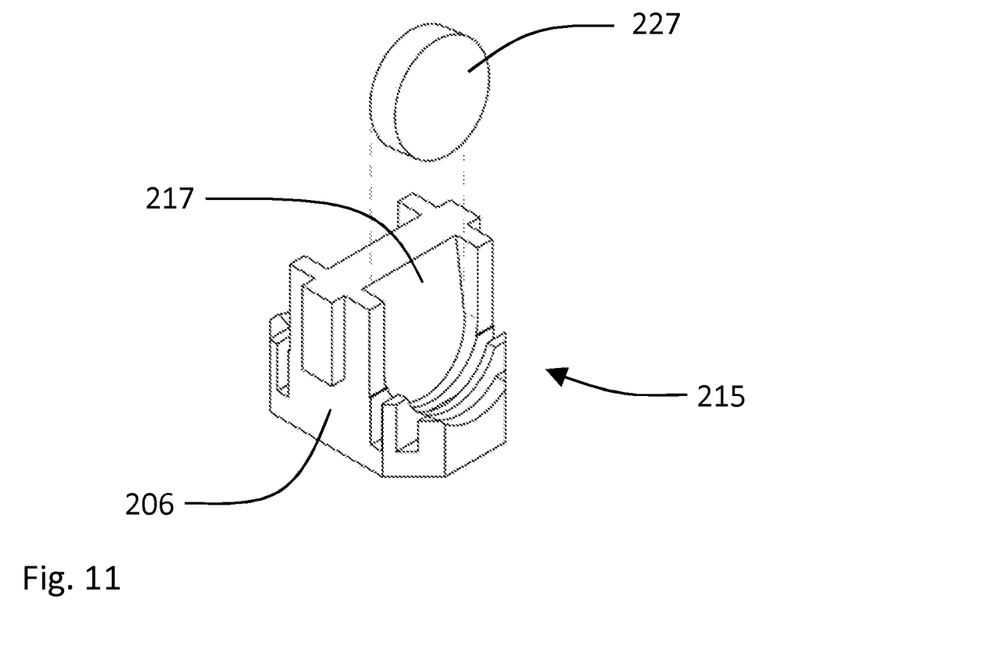
FIG. 11 the guide insert of the second exemplary embodiment of the device for preparing a bone transplant with a bone transplant in perspective view.

By way of example, FIG. 11 visualises the relationship between the shape of the guide insert 206 and an extracted bone transplant on one side of the guide insert 206 only. These relationships are transferable to all the other usable sides of the guide insert. In this context, the bone transplant 227 is a cylindrical disc of bone. The diameter of this bone disc is determined by a core drill which is used for extracting bone, e.g. from the humeral head, and it is adapted to the joint implant to be inserted. The circular surfaces of the bone transplant 227 are aligned with its cylindrical wall through the extraction process. The semi-circular recess 215 of the guide insert 206 has a diameter corresponding to the bone transplant 227. The wall of the semi-circular recess 215 and the associated contact surface 217 are disposed perpendicular to one another, corresponding of the bone transplant. Through the semi-circular embodiment of the recess 215, it is possible to insert the bone transplant 227, as shown in FIG. 11, into the guide insert 206. This can also be implemented with an assembled device 200 for preparing a bone transplant 227.

Figure 12:
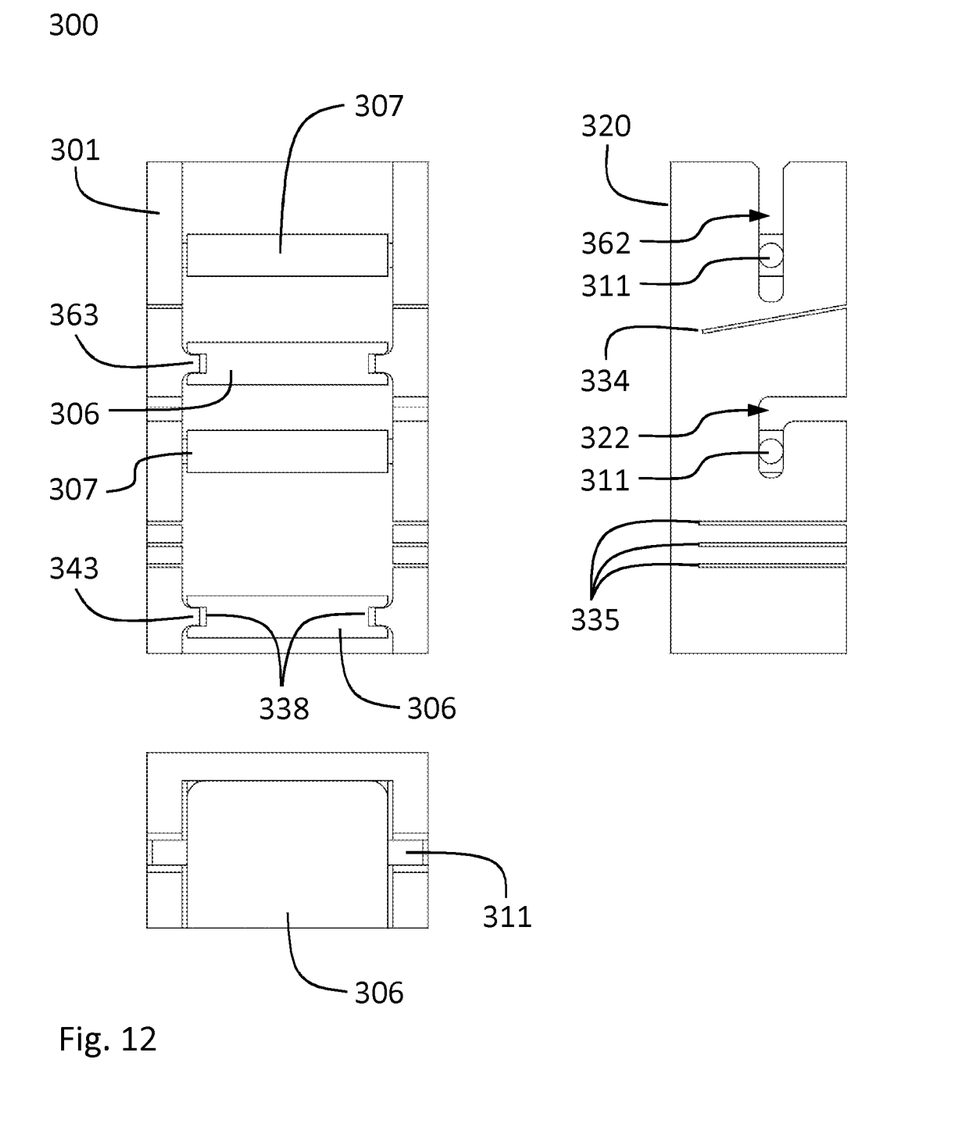
FIG. 12 a third exemplary embodiment of the device according to the invention for preparing a bone transplant with a guide insert and a holding insert in the 3-view projection.

FIG. 12 shows a third exemplary embodiment of the device according to the invention for preparing a bone transplant 300 with a base element, a guide insert 306 and a holding insert 307 in 3-view projection. The front view shown illustrates the device for preparing a bone transplant 300 from above.

The base element 301 contains, on one hand, three slots 335 extending perpendicular to the support surface 320 of the base element 301. On the other hand, the base element 301 contains one slot 334 extending diagonally. In this context, the angle relates to the guide insert 306 inserted into the base element 301. The slots 334, 335 are embodied in such a manner that a material-removing tool is guided precisely within them. The number of slots 334, 335, illustrated by way of example in FIG. 13, can vary dependent upon requirements. In this third exemplary embodiment, bone fragments can be prepared with three different lengths and with an angle defined by the diagonally extending slot 334. Dependent upon the requirements for the bone transplant, the angle of the diagonally extending slot 334 can comprise an angle between 0° and 45°. In this exemplary embodiment the angle of the diagonally extending slot 334 is 10°.

The base element 301 contains two guide recesses 343, 363. The guide recesses 343, 363 are used for guiding the guide insert 306. To ensure a displaceable guiding of the guide insert 306 in one of the guide recesses 343, 363, the guide insert 306 contains recesses 338, which correspond with the guide recesses 343, 363. The first guide recess 343 is used if the bone fragment to be prepared is to be shortened to the length required for the bone transplant. If a surface of the bone fragment to be prepared must be prepared with an angle, the guide insert 306 is inserted into the second guide recess 363.

Furthermore, FIG. 12 shows slot-shaped recesses 322, 362 in the base element 301. These slot-shaped recesses 322, 362 are embodied for the guiding of the holding insert 307. The holding insert 307 contains cylindrical pegs 311. The cylindrical pegs 311 are embodied in their diameter in such a manner that they produce a displaceable guide. In this context, the displaceable guide is embodied in such a manner that unnecessary play does not impair the precision of the device for preparing a bone transplant.

The first slot-shaped recess 322 is embodied in an L-shape. The L-shape allows the holding insert 307 to be introduced into the base element 301 from above. By means of the holding insert 307, the bone fragment to be prepared is pressed against the guide insert 306. In this context, the guide insert 306 is pushed into the position in the guide recess 343 for shortening the bone fragment. A second slot-shaped recess 362 is embodied from one end of the base element 301. Here, the holding insert 307 is introduced from the corresponding end into the base element 301. The guide insert 306 is inserted into the guide recess 363 in the position for preparing an angle on the bone fragment. By means of the holding insert 307, the bone fragment to be prepared is pressed against the guide insert 306 inserted in the guide recess 363.

The base element 301, the holding insert 306 and/or the guide insert 307 of the device for preparing a bone transplant 300 are made of metal or synthetic material. By preference, the base element 301, the holding insert 306 and/or the guide insert 307 are made from a stainless steel. If the base element 301, the holding insert 306 and/or the guide insert 307 are made from a synthetic material, a PA (polyamide), a PEEK (polyether ether ketone), a PPSU (polyphenylene sulfone) or a POM-C (polyoxymethylene copolymer) is used by preference. These materials are named only by way of example do not restrict the possible choice of materials.

Figure 13:
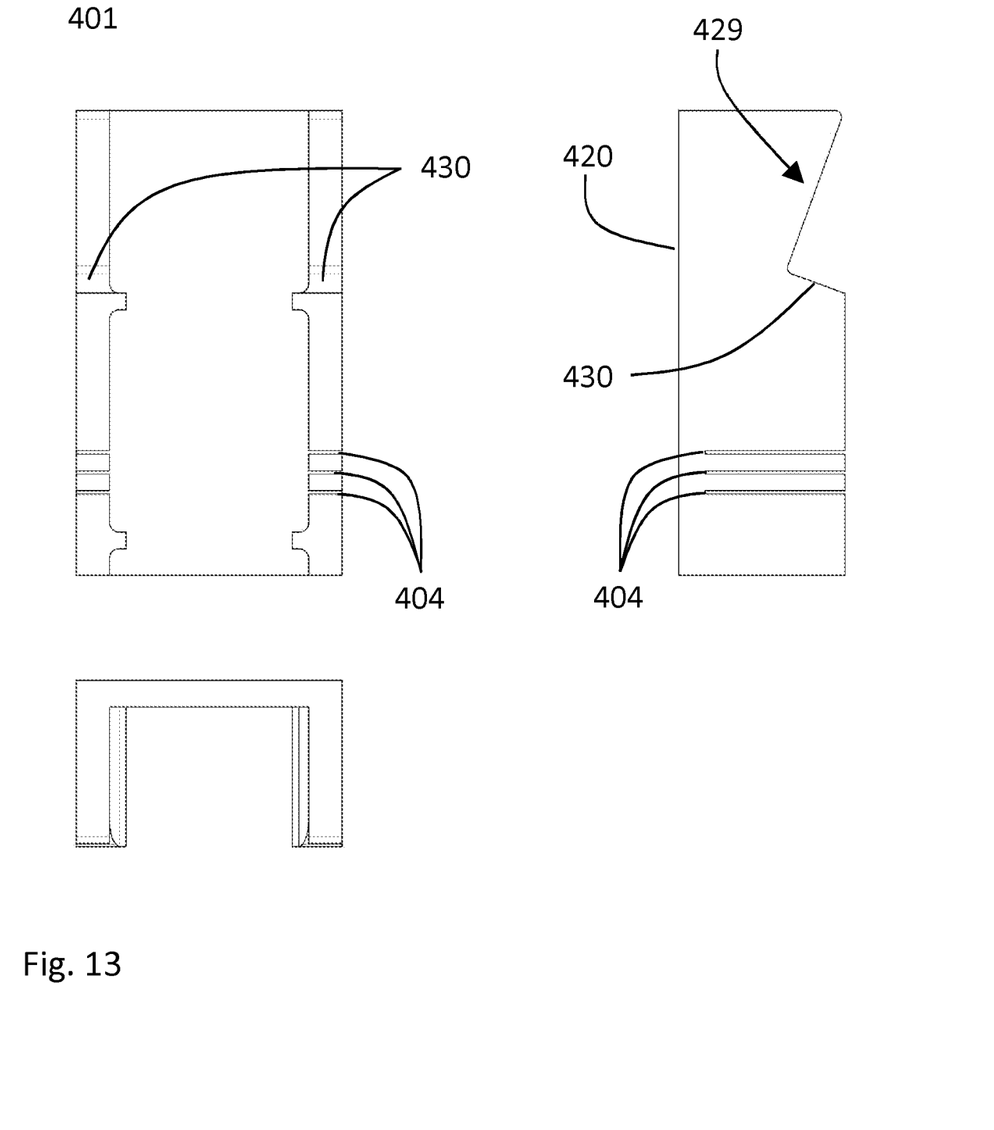
FIG. 13 a base element of a fourth exemplary embodiment of the device for preparing a bone transplant in 3-view projection.

FIG. 13 shows a base element 401 of a fourth exemplary embodiment of the device for preparing a bone transplant in 3-view projection. In the lateral view, the base element 401 is shown with three slots 404, wherein the number of slots 404 is not restricted to three. These slots 404 extend perpendicular to the support surface 420 of the base element 401. By means of the slot 404, a bone transplant can be produced with the required thickness. The thickness of the bone transplant is determined by the preparer selecting one of the slots 404 with an appropriate spacing distance from the guide insert (not shown here).

Furthermore, the base element 401 contains a region for preparing a sloping surface 429 on the bone transplant. For the preparation of a sloping surface 429, a flat surface 430 is implied. This flat surface 430 is used to guide the material-removing tool and is provided perpendicular to the support surface 420 of the base element 401 with an angle. Dependent upon the requirements for the bone transplant, the angle of the flat surface 430 comprises an angle between 0° and 45°. In the base element 201 in this exemplary embodiment, the flat surface 430 preferably has an angle of 20°.

The base element 401 of the device for preparing a bone transplant of the fourth exemplary embodiment is made from a metal or synthetic material. By preference, the base element 401 is made from a stainless steel. If the base element is made from synthetic material, a PA (polyamide), a PEEK (polyether ether ketone), a PPSU (polyphenylene sulfone) or a POM-C (polyoxymethylene copolymer) is used by preference. These materials are named only by way of example do not restrict the possible choice of materials.

Figure 14:
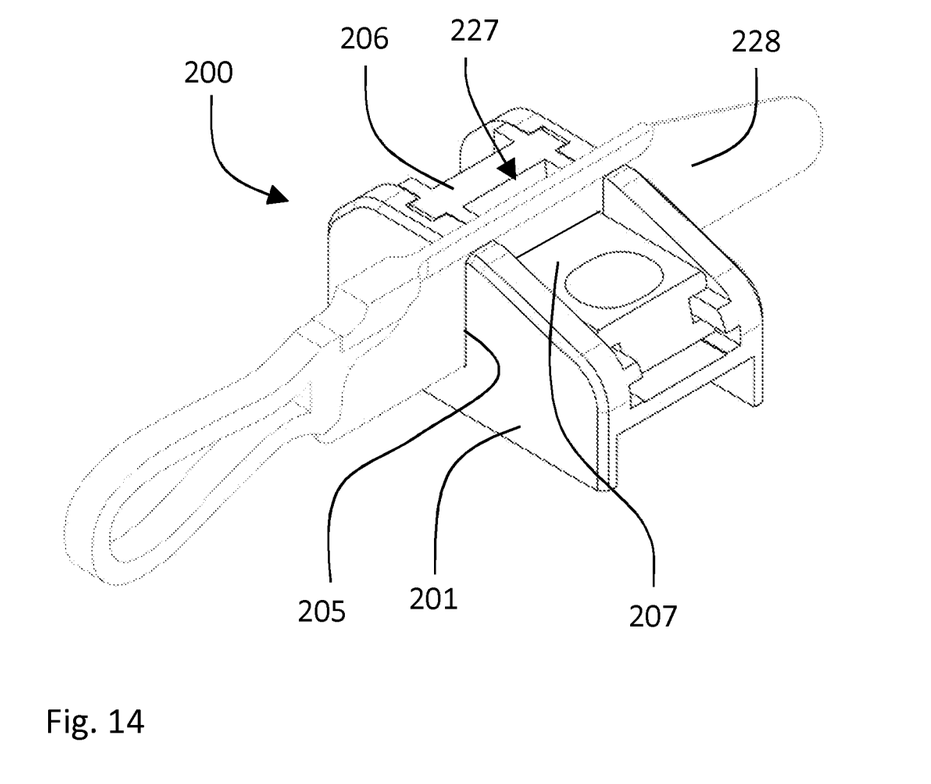
FIG. 14 the use of the device according to the invention for preparing a bone transplant.

FIG. 14 shows the use of the device according to the invention for preparing a bone transplant 100, 200 in an example. In the device according to the invention and the associated method, a bone transplant 227 is used outside the human or animal body. The so-called "back table preparation" with its specific advantages is used here. Preparation outside the patient's body on the "back table" achieves a considerable increase in the precision of the prepared bone transplant 227. Furthermore, the stress on the patient is substantially reduced, because the region from which the bone transplant 227 is removed need not be orientated in such a manner that an accurate cutting as possible and, therefore, further stress on the muscle and tendon apparatus is avoided.

As shown in FIG. 14, the bone transplant 227 is fixed in the device for preparing a bone transplant 200 by means of the guide insert 206 inserted into the base element 201 and the holding insert 207 inserted into the base element 201. With a material-removing tool 228, here, a hand saw, the bone transplant 227 to be prepared is cut to size. For this purpose, the material-removing tool 228 is introduced into the slot 205 of the base element 201 which specifies the length provided for the bone transplant 227. The bone transplant 227 is now cut to length. When the preparation process is completed, the bone transplant 227 is removed from the device for preparing a bone transplant 200. The bone transplant 227 is now available in the shape required for further use.

The device for preparing a bone transplant 200 is then dismantled, cleaned and disinfected. Through the unique construction of the device for preparing a bone transplant 200, the cleaning and disinfection process can be implemented with extraordinarily high process security.

All the features described and/or illustrated can be advantageously combined with one another within the scope of the invention. The invention is not restricted to the exemplary embodiments described.

The invention claimed is:

1. A device for preparing a bone graft outside of a human or animal body, the device comprising:
   a base element, wherein the base element includes a support surface and at least one slot bounded by slot surfaces that extend perpendicular to the support surface, the at least one slot for guiding a cutting tool;
   a guide insert comprising a first contact surface configured to contact the bone graft, wherein the guide insert is configured to be inserted into the base element, and wherein when the guide insert is inserted into the base element a first non-zero angle between the first contact surface and the slot surfaces is defined in a plane perpendicular to both the slot surfaces and the support surface; and
   a holding insert comprising a first holding surface configured to contact the bone graft, wherein the holding insert is configured to be inserted into the base element, and wherein when the holding insert is inserted into the base element, a second non-zero angle between the first holding surface and the slot surfaces is defined in the plane.

2. The device for preparing a bone graft of claim 1, wherein the guide insert and the holding insert are embodied geometrically differently, wherein the base element comprises two guide recesses for receiving the guide insert and wherein the base element further comprises two rails for receiving the holding insert.

3. The device for preparing a bone graft of claim 1, wherein the holding insert contains at least one finger recess.

4. The device for preparing a bone graft of claim 1, wherein the guide insert further comprises a semi-circular or semi-cylindrical recess for receiving the bone graft, wherein an axis of the semi-circular or semi-cylindrical recess is arranged at a right angle to the first contact surface of the guide insert.

5. The device for preparing a bone graft of claim 1, wherein the first non-zero angle is equal to the second non-zero angle.

6. The device for preparing a bone graft of claim 5, wherein each of the first and second non-zero angles is about 7.5 degrees.

7. A method for configuration of the device for preparing a bone transplant outside the human or animal body according to claim 1, wherein the holding insert is inserted into the base element.

8. The method for configuration of the device for preparing a bone transplant according to claim 7, wherein the guide insert is inserted into the base element.

9. The device for preparing a bone graft of claim 1, wherein the guide insert further comprises a second contact surface configured to contact the bone graft, wherein when the guide insert is inserted into the base element, a third non-zero angle between the second contact surface and the slot surfaces is defined in the plane, wherein the holding insert further comprises a second holding surface configured to contact the bone graft, and wherein when the holding insert is inserted into the base element, a fourth non-zero angle between the second holding surface and the slot surfaces is defined in the plane.

10. The device for preparing a bone graft of claim 9, wherein the first contact surface and the second contact surface are arranged on opposite sides of the guide insert.

11. The device for preparing a bone graft of claim 9, wherein the guide insert further comprises a semi-circular or semi-cylindrical recess for receiving the bone graft, wherein an axis of the semi-circular or semi-cylindrical recess is arranged at a right angle to the second contact surface of the guide insert.

12. The device for preparing a bone graft of claim 9, wherein the third non-zero angle is equal to the fourth non-zero angle.

13. The device for preparing a bone graft of claim 12, wherein each of the third and fourth non-zero angles is about 15 degrees.

* * * * *